United States Patent
Yamaguchi

[11] Patent Number: 5,968,555
[45] Date of Patent: Oct. 19, 1999

[54] FINE PARTICULATE CROSS-LINKED TYPE N-VINYLAMIDE RESIN

[75] Inventor: Tetsuhiko Yamaguchi, Kawasaki, Japan

[73] Assignee: Showa Denko K.K., Tokyo, Japan

[21] Appl. No.: 09/001,924

[22] Filed: Dec. 31, 1997

[30] Foreign Application Priority Data

Feb. 17, 1997 [JP] Japan ................................ 9-032124

[51] Int. Cl.$^6$ ................. A61K 9/16; A61K 9/10; A61K 47/32; A01N 25/12

[52] U.S. Cl. .................. 424/501; 424/487; 514/944; 514/952

[58] Field of Search ................. 424/487, 501; 514/944, 952, 772.6; 428/402; 252/315.4; 526/318.42, 30; 525/330.3, 328.2

[56] References Cited

U.S. PATENT DOCUMENTS

| | | |
|---|---|---|
| 4,123,275 | 10/1978 | Karino et al. . |
| 4,268,604 | 5/1981 | Yoshida et al. . |
| 4,396,706 | 8/1983 | Ishii et al. . |
| 5,280,095 | 1/1994 | Aizawa et al. ................. 526/307.6 |
| 5,338,815 | 8/1994 | Aizawa et al. . |
| 5,599,898 | 2/1997 | Hartmann et al. . |

FOREIGN PATENT DOCUMENTS 4-323213  11/1992  Japan ............................ C08F 226/02

*Primary Examiner*—Edward J. Webman
*Attorney, Agent, or Firm*—Sughrue, Mion, Zinn, Macpeak & Seas, PLLC

[57] ABSTRACT

A fine particulate cross-linked N-vinylamide resin having an average particle size of not more than 10 $\mu$m comprising a compound (I) and a compound (II) cross-linked by a cross-linking agent:

$$CH_2 = CR^1NR^2COR^3 \quad (I)$$

$$CH_2 = CR^4 - \underset{\underset{O}{\|}}{C} - (OX)_n - OR^5 \quad (II)$$

wherein, $R^1$ to $R^5$ may be the same or different and represent a hydrogen atom, methyl group, or ethyl group, X is a $C_2$ or $C_3$ alkylene group, and n is an integer of 2 to 30 and the weight ratio of (I):(II) is 70 to 99.9:30 to 0.1, and the microgel composed thereof.

7 Claims, No Drawings

FINE PARTICULATE CROSS-LINKED TYPE N-VINYLAMIDE RESIN

BACKGROUND OF THE INVENTION

1. Field of the Invention

The present invention relates to a fine particulate cross-linked type N-vinylamide resin (i.e., same meaning as N-vinylcarboxylic acid amide resin), a process for producing the same, a microgel composed of the cross-linked type N-vinylamide resin comprising that resin swelled or gelled with water or an organic solvent, and a thickener, dispersion stabilizer, or lubricant comprising that microgel as a main component. More specifically, the present invention relates to a fine particulate cross-linked type N-vinylcarboxylic acid amide resin having an excellent chemical stability and affinity for water and organic solvents such as alcohols, particularly exhibiting a high thickening ability, dispersion stability, and lubricity without being affected by an electrolyte solution in which inorganic or organic ions coexist in the system, a microgel having a wide usage in various fields due to the excellent characteristics and functions of the resin, and a hydrophilic thickener, or a thickener having an additionally added organic solvent affinity dispersion stabilizer, or lubricant comprising the microgel as the main component.

2. Description of the Related Art

In the prior art, fine particles of a cross-linked hydrophilic gel exist as a dispersion of swelled fine particles in water unlike a water-soluble linear polymer which exists as a solution in water. The dispersion thereof exhibits a non-Newtonian flow even at a low concentration and exhibits a remarkably high viscosity, as is widely known in the art. It has been variously utilized as a thickener, dispersion stabilizer, and lubricant for aqueous gel-like products, textile size, and cosmetics.

As the cross-linked type fine particles known in the art, for example, synthetic polymers such as cross-linked type polyacrylic acid (carboxyvinyl polymer) and cross-linked type acrylic acid copolymer may be included. These cross-linked type fine particles, however, are all cross-linked products of the polymeric electrolyte type, and therefore, exhibit an excellent thickening ability for water containing no electrolyte but exhibit only remarkably low thickening ability for an aqueous liquid containing a large amount of organic or inorganic ions, such as a natural extract, surfactant, perfume, colorant, reactive dye for printing, and cement slurry. This is considered to be a result of a reduced expansion of the chains because of a suppression of dissociation of the polymeric electrolyte, which is the backbone chain of the cross-linked product, in the presence of ions. Further, when polyvalent metal ions exist, ion cross-linking occurs through the backbone carboxylic acid, whereby a cross-linked polymer with a substantially higher cross-linking density than required is formed, which lowers the thickening ability.

To overcome the drawback mentioned above, Japanese Unexamined Patent Publication (Kokai) No. 4-323213 discloses a non-ionic thickener substantially free from the effect of electrolytes comprising a fine particulate cross-linked type N-vinylcarboxylic acid amide resin. This thickener is improved in regard to the defect of the above polymeric electrolyte thickener, that is, the reduction of the thickening ability in an electrolyte solution, but since it is non-ionic, requires a larger amount of resin to be added to obtain a high viscosity liquid and therefore causes a drop in the feeling of use in cosmetics etc.

In water absorbing resins known in the art, an aqueous dispersion thereof exhibits viscosity, but because of the greater particle size, the system as a whole becomes non-uniform and therefore does not exhibit a thixotropic viscous behavior.

Further, among natural polymers, such as those which are not fine particles but exhibit a viscous behavior similar to the cross-linked type fine particles, there may be included natural gums such as gum tragacanth, locust bingham, sodium alginate, carrageenan, and guar gum. These natural polymers, although they contain the groups of electrolytes, exhibit a relatively good thickening ability also for an aqueous liquid containing a large amount of ions. Natural polymers, however, not only fluctuate in cost, but also are susceptible to attack by microorganisms, bringing the problem of corruption, and have a peculiar color and odor, thus the scope of use thereof is limited.

SUMMARY OF THE INVENTION

Accordingly, the object of the present invention is to provide a novel water-soluble polymer which has a high thickening ability in a liquid (e.g., electrolyte solution) wherein inorganic or organic ions coexist, is chemically stable, has affinity to even polar solvents such as alcohols, and raises the yield value to improve the apparent thickening ability.

In accordance with the present invention, there are provided a fine particulate cross-linked type N-vinylamide resin having an average particle size of not more than 10 μm comprising cross-linked copolymer of a compound having the formula (I) and a compound having the formula (II):

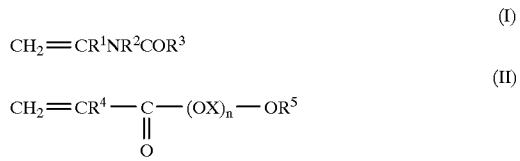

wherein, $R^1$ to $R^5$ may be the same or different and represent a hydrogen atom, methyl group, or ethyl group, X is a $C_2$ or $C_3$ alkylene group, and n is an integer of 2 to 30 and the weight ratio of (I):(II) is 70 to 99.9:30 to 0.1, preferably 75 to 95:25 to 5, a microgel comprising a cross-linked type N-vinylamide resin composed of said resin gelled with water or an organic solvent, and a thickener, dispersion stabilizer, or lubricant comprising said microgel as a main ingredient.

Further, in accordance with the present invention, there is provided a process for producing a fine particulate cross-linked type N-vinylamide resin having an average particle size of not more than 10 μm comprising the step of: precipitation copolymerizing 70 to 99.9% by weight of the compound having the formula (I) and 0.1 to 30% by weight of the compound having the formula (II) in an organic solvent which uniformly dissolve the reaction components at the start of the reaction and in the presence of a cross-linking agent.

DESCRIPTION OF THE PREFERRED EMBODIMENTS

The present invention will be described in further detail below.

The compounds having the formula (I) used in the present invention include, for example, N-vinylformamide, N-vinylacetamide, N-methyl-N-vinyl-formamide, N-methyl-N-vinylacetamide, N-vinylpropion-amide, etc., and N-vinylacetamide is particularly preferable.

Further, the compound having the formula (II) include, for example, those where X is —CH$_2$CH$_2$—, —CH$_2$CH(CH$_3$)—, or —CH$_2$CH$_2$CH$_2$—. Examples thereof are methoxydiethylene glycol methacrylate, methoxytriethylene glycol methacrylate, methoxytripropylene glycol acrylate, methoxypolyethylene glycol methacrylate (n=4–30), diethylene glycol monomethacrylate, triethylene glycol monomethacrylate, polyethylene glycol monomethacrylate (n=4–30), methoxydiethylene glycol acrylate, methoxytriethylene glycol acrylate, methoxypolyethylene glycol acrylate (n=4–30), diethylene glycol monoacrylate, triethylene glycol monoacrylate, and polyethylene glycol monoacrylate (n=4–30). Among these, ones where the X of the general formula (II) is an ethylene group (—CH$_2$CH$_2$—) are preferred, particularly, methoxypolyethylene glycol methacrylate (n=4–30) is preferred.

The compound having the formula (I) must be contained in an amount of at least 70% by weight of the total of the compound of the general formula (I) and the compound of the general formula (II). Below this, the specific features of the microgel according to the present invention, that is, the thickening ability of alcohol etc. and the light resistance, are not sufficiently manifested. In particular, when the thickening ability of alcohol etc. and the light resistance are emphasized, it is preferably contained in an amount of at least 80% by weight, more preferably at least 85% by weight. The compound having the formula (II) must be contained in an amount of at least 0.1% by weight of the total of the compound having the formula (I) and the compound having the formula (II). Below this, the effect of improvement in the yield value is not obtained. In particular, when the thickening ability and suitable fiber forming ability are emphasized, it is preferably contained in an amount of at least 0.3% by weight. Further, when contained in an amount more than 30% by weight, the fiber forming ability becomes too great and the thixotropic property inherently obtained from the microgel becomes inferior.

Each one of the compound having the formula (I) and the compound having the formula (II) may be used alone, but two or more compounds of the formula (I) or the formula (II) may be used as well. Further, so long as the object of the present invention is not impaired, it is possible to use another ethylenic unsaturated compound as a monomer, in addition to the compound having the formula (I) and the compound having the formula (II). The fine particulate cross-linked type N-vinylamide resin thus obtained is included in the resins of the present invention. In this case, the other ethylenic unsaturated compound must not be contained in an amount exceeding 0.1 part by weight, based upon 1 part by weight of the compound having the formula (I) and the compound having the formula (II).

The oxyethylene glycol units included in the monomer of the compound having the formula (II) contribute to the increase of the solubility in water and the thickening ability compared with the case of the cross-linked homopolymer of the compound having the formula (I).

The "yield value" used herein means the shear stress when the aqueous solution starts to flow when applying stress to the aqueous solution of the resin and may be measured by a rheometer etc.

The cross-linking agents usable in the present invention are compounds having at least two unsaturated polymerizable groups in one molecule. Representative specific examples thereof are shown below.

N,N'-methylene bisacrylamide, ethylene glycol di(meth)acrylate, diethylene glycol di(meth)acrylate, triethylene glycol di(meth)acrylate, polyethylene glycol di(meth)acrylate, trimethylol propane tri(meth)acrylate, pentaerythritol tri(meth)acrylate, divinylbenzene, divinyl ether, tetraallyloxyethane, pentaerythritol triallyl ether, triallyl phosphate, trimethylolpropane diallyl ether, allyl sucrose, N,N'-butylene bis(N-vinylacetoamide), N,N'-hexylene bis(N-vinylacetoamide), N,N'-butylene bis(N-vinylformamide), N,N'-(diacetyl)-N,N'-(divinyl)-1,3-bis(aminomethyl)cyclohexane, and other compounds having two or more ethylenic unsaturated groups in a molecule, but the invention is not limited to these. Among these, divinylbenzene, tetraallyl oxyethane, pentaerythritol triallyl ether, trimethylolpropane diallyl ether, N,N'-(diacetyl)-N,N'-(divinyl)-1,3-bis (aminomethyl) cyclohexane, etc. are preferable.

The amount of the cross-linking agent to be used in the present invention is not particularly limited, but is generally 0.01 to 10 mole %, preferably 0.1 to 6.0 mole %, more preferably 0.5 to 4.0 mole %, based on the total of the compound having the formula (I) and the compound having the formula (II) so as to give a cross-linking density of 1/10 to 1/10,000, preferably 1/50 to 1/1000. In this connection, if the amount of the cross-linking agent used is more than 10 mole %, the cross-linking density of the resin obtained becomes too high, whereby the swelling ratio will be remarkably lowered and the desired thickening effect will not be exhibited. On the other hand, if it is less than 0.01 mole %, the ratio of the polymer chains not cross-linked will be increased, whereby the resin becomes readily soluble in water or an organic solvent to exhibit a greater fiber forming property, and thus does not have a thixotropic property as the thickener.

The amount of the cross-linking agent used is considerably larger than that of the cross-linked hydrophilic resins in general, but this is necessary for obtaining the desired cross-linking density. However, in the microgel of the present invention, since the particles are fine, no gelatin-like mass is formed and a good flow characteristic can be exhibited in spite of the high cross-linking density thereof.

As the process for producing the fine particulate cross-linked N-vinylamide resin according to the present invention, the precipitation polymerization process can be employed. The process comprises dissolving the monomer components and the cross-linking agent in an organic solvent, thoroughly removing the dissolved oxygen and elevating the temperature to a reaction temperature. Further, in the sense of removing the oxygen, polymerization may be performed at the boiling point of the polymerization solution used. Then, an initiator is added to carry out the reaction, and the resin formed with the progress of the reaction is precipitated as fine particles in the solvent. By filtration, drying, and disagglomeration (i.e., the secondary agglomerated particles are disintegrated to the primary particles) of the resin, a fine particulate resin is obtained.

The cross-linked type N-vinylamide fine particles are produced by this polymerization method because, unlike with powder type products obtained by drying and pulverizing a gel obtained by the aqueous solution polymerization method used for producing usual water absorbing resins etc. or bead type products obtained by the reverse phase suspension polymerization method, the formation of the extremely fine powder product (microgel) obtained by precipitation polymerization in the above organic solvent enables a thickening ability to be achieved in water or an organic solvent.

The reaction solvent usable in the present invention is not necessarily required to uniformly dissolve the reaction components at room temperature, but uniformly dissolves the reaction components (i.e., monomer components and cross-linking agent) upon initiation of the reaction, and further in which the resin formed is insoluble, but a non-aqueous solvent generally stable during a radical polymerization may be employed without particular limitation. Representative specific examples thereof are set forth below.

Aromatic or aliphatic hydrocarbons such as benzene, toluene, xylene, hexane, heptane, octane, or the like, aliphatic ketones such as acetone, methyl ethyl ketone, methyl isobutyl ketone, or the like, esters such as ethyl acetate, butyl acetate, isopropyl acetate, or the like, alkyl amides such as dimethylformamide, dimethylacetamide, or the like, sulfoxides such as dimethylsulfoxide or the like, and so on. Among the above, it is particularly preferable to use benzene, acetone, methyl ethyl ketone, ethyl acetate, isopropyl acetate, etc.

As the polymerization initiator, peroxides, organic peracids, and azobis type compounds which can be uniformly dissolved in the solvent may be employed. The representative examples are as shown below.

Benzoyl peroxide, t-butyl peroxide, t-amyl peroxide, cumyl peroxide, lauroyl peroxide, t-butyl hydroperoxide, cyclohexyl hydroperoxide, tetralin hydroperoxide, t-butyl peracetate, bis(2-ethylhexylper oxydicarbonate), 2,2'-azobis-i-butyronitrile, phenylazotriphenyl-methane, 2,2'-azobis(4-methoxy-2,4-dimethylvaleronitrile), 2,2'-azobis (2-methylpropionitrile), 2,2'-azobis(2-methylbutyronitrile), 1,1'-azobis(cyclohexane-1-carbonitrile), and dimethyl-2,2'-azobis(2-methylpropionate) may be mentioned.

Among the above, particularly the use of benzoyl peroxide, 2,2'-azobis-i-butyronitrile, dimethyl-2,2'-azobis (2-methylpropionate), etc. is preferred.

The amount of the polymerization initiator to be used in the present invention is not particularly limited, but may be, for example, 0.01 to 5 mole % based on the total of the compound of the general formula (I) and the compound of the general formula (II) (monomer components). Other reaction conditions also are not particularly limited, but may be as generally described below.

The amount of solvent employed in the present invention is anywhere from an equivalent amount to 20-fold the amount of the monomers, preferably 5-fold to 15-fold, particularly preferably 5-fold to 10-fold (weight) of the monomers. The polymerization initiation temperature is suitably from 50° C. to the boiling point of the solvent. The reaction time is about 3 to 8 hours.

The cross-linked type N-vinylamide resin obtained by the precipitation polymerization method in this way has a particle size of not more than 10 $\mu$m, usually not more than several $\mu$m. Since its molecular weight, the cross-linking density, and the particle size are suitably controlled, the optimum thickening ability, dispersion stabilization ability, and lubrication ability in water and an organic solvent can be exhibited. Further, in the precipitation polymerization method, since the polymer is obtained as a precipitate in an organic solvent, the polymer can be easily obtained in a powder state by filtration etc.

The viscosity of the resultant resin is preferably 100–3000 mPa.s, determined by a Brookfield rotational viscometer when 1% of the resin is dispersed and swelled in deionized water. In view of the fact that the high viscosity liquid according to the present invention is obtained, the viscosity of 400–3000 mPa.s is more preferable. When the viscosity is more than 3000 mPa.s, the fiber forming property becomes undesirably strong and the thixotropic property becomes undesirably poor, although the high viscosity liquid is obtained. On the other hand, when the viscosity is less than 100 mPa.s, the thickening property is decreased, and therefore, the necessary amount thereof to be added to various liquid formulations is unpreferably increased so that the other properties of the formulations are sometimes adversely affected. Furthermore, in the case of the cross-linked type homo N-vinylamide resin, only those having a viscosity of 400 mPa.s or less can be obtained, the viscosity of 400 mPa.s or more can be easily obtained according to the present invention.

The N-vinylamide polymer according to the present invention is effective even with respect to various aqueous solutions including inorganic salts etc. since there is no reduction in viscosity even when sodium chloride, calcium chloride, etc. is added. Further, it has affinity with respect to organic solvents including alcohols such as methanol, ethanol, isopropyl alcohol, benzyl alcohol, and polyols such as ethylene glycol, propylene glycol, glycerol and can thicken these liquids. In addition, it is superior in chemical stability. The polymer can be used for various applications using its thickening effect, dispersion effect, and other functions. Specific examples are given as follows:

(1) Cosmetics, for example, emulsion stabilizers, thickeners, and lubricants of cosmetics such as shampoos, rinses, and lotions, emulsion type cosmetics (used as emulsifiers), film type packs, and salt-containing cosmetics.

(2) Medical field, for example, for the holding and sustained release of drugs, for example, tablets (sustained release drugs), drugs for absorption in the intestines, substrates for pap agents, ointments, preparations for control of the release of drugs, preparations for sustained release in the stomach, preparations for absorption through the mucous membrane, compositions for outer coatings (medical film), protective materials for covering wounds, oral materials (dental materials, oral-use absorbents, and flossing agents), lubricants for urinary catheters, enemators, and other medical devices heated by a disinfecting autoclave for repeated use, and viscosity adjusters for diagnostics.

(3) Household products, such as liquid detergents (for apparel, the kitchen, toilet, and tile), toothpaste, cleansers, and softeners.

(4) Agricultural and horticultural applications, for example, seed germination and growth promoters (for example, sowing promoters for seeds of vegetables, flowers, etc., germination promoters for seeds, and seed coating agents), growth media for plants (for example, seedling beds, soil improvers, plant cultivation humectants, incubation media for microorganisms etc.), methods of administration of chemicals to plants (for example, devices for administration of chemicals to trunks, agents for the sustained release of agrochemicals), and others (for example, coverings for protection from frost and materials for preventing formation of dew).

(5) Industrial use thickeners, for example, printing sizes (printing sizes using reactive dyes, dispersion dyes, mordant dyes, etc.), carpet packing sizes, warp sizes, emulsion paints, water-soluble inks, and water-soluble ballpen inks.

(6) Tackifiers and their aids.

(7) Civil engineering and construction use, for example, greenification of steep slopes and soil improvers.

(8) Others, for example, fresheners and deodorants, inorganic salt solution type absorbants, desiccants, fermentation aids, packing materials, water swelling paints, antifouling coatings for ship bottoms, release agents for old wallpaper etc., core materials for golf balls, toys, sweat absorbers, contact media for ultrasonic flaw detection, contacts for ultrasonic detectors, and electrolyte supports for batteries and sensors.

As explained above, the fine particle cross-linked type N-vinylamide resin according to the present invention or its microgel can be suitably used in a wide range of fields.

EXAMPLES

The present invention will now be explained in more detail with reference to the Examples and Comparative Examples, which in no way limit the scope of the present invention. Note that in the Examples and Comparative Examples, "parts" indicate "parts by weight" unless otherwise indicated.

Example 1

90 parts of N-vinylacetoamide, 10 parts of methoxypolyethylene glycol methacrylate (n=30), and 1.5 parts of pentaerythritol triallyl ether were dissolved in 900 parts of ethyl acetate. This was made to boil and then 1.0 part of dimethyl-2,2'-azobis(2-methylpropionate) was added as the radical polymerization initiator and the boiling state was maintained. Along with the progress of the polymerization, the cross-linked type N-vinylamide resin polymer formed was precipitated into the ethyl acetate, so this state was held as it was for 5 hours. The solution was then allowed to cool, then the polymer was removed by suction filtration, vacuum dried at 50° C. for 24 hours, and macerated to obtain 98 parts of a fine particulate cross-linked type N-vinylamide resin with a particle size of not more than 5 μm.

The performance of the resin was evaluated in terms of the viscosity of a 1% deionized water dispersion near the neutral point (pH 6 to 8). The results are shown in Table 1. Further, the salt resistance when sodium chloride was added to the dispersion was evaluated by the viscosity.

The obtained resin was dispersed in polar solvents such as methanol, ethanol, benzyl alcohol, and glycerin to obtain transparent gel-like products.

Method of Measuring Viscosity of Deionized Water Dispersion

Into a 200 ml tall beaker was charged 198 g of refined water. 2 g of the resin obtained in the Example was dispersed and dissolved therein with vigorous stirring so that no mass was formed. The viscosity of the 1% deionized water dispersion thus obtained was measured by using a Brookfield type single rotor rotational viscometer with SB type spindle #2 under the condition of 20° C. according to a JIS K7117 method.

Salt Resistance Test

In the 1% deionized water dispersion prepared according to the deionized water dispersion viscosity measuring method, NaCl was added and dissolved to give a solid concentration in the liquid of 5% and the viscosity was measured.

Example 2

The reaction was carried out by the same procedure as in Example 1, except that methoxypolyethylene glycol acrylate (n=9) was used in place of methoxy-polyethylene glycol methacrylate (n=30), to obtain a fine particulate resin. The thickening ability and the results of the salt resistance test are shown in Table 1.

The affinity with a polar solvent was similar to that of Example 1.

Example 3

The reaction was carried out by the same procedure as in Example 1, except that 2.0 parts of divinylbenzene was used in place of the 1.5 parts of pentaerythritol triallyl ether and benzene was used in place of the ethyl acetate as the polymerization solvent, to obtain a fine particulate resin in the same way as in Example 1. The thickening ability and the results of the salt resistance test are shown in Table 1.

The affinity with a polar solvent was similar to that of Example 1.

Example 4

75 parts of N-vinylacetamide, 25 parts of methoxypolyethylene glycol methacrylate, and 1.5 parts of tetraallyloxyethane were dissolved in 900 parts of ethyl acetate. Nitrogen was bubbled through this and the temperature raised to 70° C., then 1.0 part of azoisobutyronitrile was added as the radical polymerization initiator and the 70° C. state was maintained. Along with the progress of the polymerization, the cross-linked type N-vinylamide resin polymer formed was precipitated into the ethyl acetate, so this state was held as it was for 5 hours. After this, the exact same procedure was followed as in Example 1 to obtain the copolymer. The thickening ability and the results of the salt resistance test are shown in Table 1.

The affinity with a polar solvent was similar to that of Example 1.

Example 5

85 parts of N-vinylformamide, 15 parts of methoxypolyethylene glycol methacrylate (n=30), and 2.5 parts of N,N'-hexylene bis(N-vinylacetoamide) were dissolved in 900 parts of ethyl acetate. Nitrogen was bubbled through this and the temperature raised to 70° C., then 1.0 part of azoisobutyronitrile was added as the radical polymerization initiator and the 70° C. state was maintained. Along with the progress of the polymerization, the cross-linked type N-vinylamide resin polymer formed was precipitated into the ethyl acetate, so this state was held as it was for 5 hours. After this, the exact same procedure was followed as in Example 1 to obtain the copolymer. The thickening ability and the results of the salt resistance test are shown in Table 1.

The affinity with a polar solvent was similar to that of Example 1.

Example 6

The reaction was carried out by the same procedure as in Example 4, except that 15 parts of tetraallyloxyethane was used, to obtain a fine particulate resin. The thickening ability and the results of the salt resistance test are shown in Table 1.

The affinity with a polar solvent was similar to that of Example 1.

Example 7

The reaction was carried out by the same procedure as in Example 1, except that 0.1 part of the pentaerythritol triallyl ether was used and 0.5 parts of 2,2'-azobisisobutyronitrile was used in place of dimethyl-2,2'-azolis (2-methylpropionate), to obtain a fine particulate resin. The thickening ability and the results of the salt resistance test are shown in Table 1.

The affinity with a polar solvent was similar to that of Example 1.

Example 8

The reaction was carried out by the same procedure as in Example 1, except that 3 parts of pentaerythritol triallyl ether and 4 parts of dimethyl-2,2'-azobis (2-methylpropionate), to obtain a fine particulate resin. The thickening ability and the results of the salt resistance test are shown in Table 1.

The affinity with a polar solvent was similar to that of Example 1.

Comparative Example 1

100 parts of N-vinylacetoamide and 1.5 parts of pentaerythritol triallyl ether were dissolved in 900 parts of ethyl acetate and the same procedure followed as in Example 1 to obtain a cross-linked N-vinylamide resin. The thickening ability and results of the acid resistance test are shown in Table 1.

Comparative Example 2

A 1% deionized water dispersion of a cross-linked polyacrylate (brandname Carbopol 940) was adjusted to pH7 by sodium hydroxide. The thickening ability and results of the acid resistance test are shown in Table 1.

TABLE 1

| Resin | Viscosity of aqueous solution (mPa·0 s) | Viscosity of aqueous solution at addition of 5% NaCl (mpa·s) |
|---|---|---|
| Example 1 | 1,200 | 1,200 |
| Example 2 | 600 | 580 |
| Example 3 | 850 | 830 |
| Example 4 | 2,000 | 1,950 |
| Example 5 | 1,000 | 1,050 |
| Example 6 | 900 | 910 |
| Example 7 | 500 | 500 |
| Example 8 | 1,000 | 990 |
| Comp. Example 1 | 250 | 245 |
| Comp. Example 2 | 70,000 | 1,000 |

The present invention provides a fine particulate cross-linked type N-vinylamide resin superior in chemical stability, having affinity to water and to alcohol and other organic solvents, and exhibiting a high thickening ability, dispersion stability, and lubricity without being effected by an electrolyte solution where inorganic or organic ions coexist in the system, microgels having broad applications in various fields making use of the superior features and functions of the resin, and hydrophilic and organic solvent-philic thickeners, dispersion stabilizers, and lubricants comprising these microgels as main ingredients.

I claim:

1. A fine particulate cross-linked N-vinylamide resin having an average particle size of not more than 10 μm comprising cross-linked copolymer of a compound having the formula (I) and a compound having the formula (II):

$$CH_2=CR^1NR^2COR^3 \quad (I)$$

$$CH_2=CR^4-\underset{\underset{O}{\|}}{C}-(OX)_n-OR^5 \quad (II)$$

wherein, $R^1$ to $R^5$ may be the same or different and represent a hydrogen atom, methyl group, or ethyl group, X represents a $C_2$ or $C_3$ alkylene group, and n is an integer of 2 to 30 and the weight ratio of (I):(II) is 70 to 99.9:30 to 0.1).

2. The fine particulate cross-linked N-vinylamide resin as claimed in claim 1, wherein $R^1$ is a hydrogen atom, $R^2$ is a hydrogen atom, $R^3$ is a hydrogen atom or methyl group, and X is an ethylene group.

3. The fine particulate cross-linked N-vinylamide resin as claimed in claim 1, wherein the cross-linking density is 1/10 to 1/10,000.

4. The fine particulate cross-linked type N-vinylamide resin as claimed in claim 1 wherein the 1% viscosity according to a Brookfield rotational viscometer when dispersed and swollen in deionized water is 100 to 3000 mPa.s.

5. A microgel comprising the fine particulate cross-linked N-vinylamide resin according to claim 1 gelled by water or an organic solvent.

6. A process for producing a fine particulate cross-linked N-vinylamide resin having an average particle size of not more than 10 μm comprising the step of precipitation copolymerizing 70 to 99.9% by weight of the compound having the formula (I) and 0.1 to 30% by weight of the compound having the formula (II):

$$CH_2=CR^1NR^2COR^3 \quad (I)$$

$$CH_2=CR^4-\underset{\underset{O}{\|}}{C}-(OX)_n-OR^5 \quad (II)$$

wherein, $R^1$ to $R^5$ may be the same or different and represent a hydrogen atom, methyl group, or ethyl group, X is a $C_2$ or $C_3$ alkylene group, and n is an integer of 2 to 30, in an organic solvent which uniformly dissolve the reaction components (I) and (II) at the start of the reaction and in the presence of a cross-linking agent.

7. A thickener, dispersion stabilizer, or lubricant comprising, as a main ingredient, the microgel according to claim 5.

* * * * *